United States Patent
Wood (10) Patent No.: US 7,122,815 B2
(45) Date of Patent: Oct. 17, 2006

(54) INFRARED RADIATION EMITTER

(76) Inventor: Donald S. Wood, 702 Monroe St., Santa Rosa, CA (US) 95404

( * ) Notice: Subject to any disclaimer, the term of this patent is extended or adjusted under 35 U.S.C. 154(b) by 0 days.

(21) Appl. No.: 10/857,140

(22) Filed: May 27, 2004

(65) Prior Publication Data

US 2004/0238763 A1 Dec. 2, 2004

Related U.S. Application Data (60) Provisional application No. 60/537,826, filed on Jan. 20, 2004, provisional application No. 60/473,498, filed on May 27, 2003.

(51) Int. Cl.
*A61N 5/06* (2006.01)
(52) U.S. Cl. ............... 250/504 R; 250/504; 250/504 H
(58) Field of Classification Search ............... 250/504, 250/504 R, 504 H, 493.1, 495.1
See application file for complete search history.

(56) References Cited

U.S. PATENT DOCUMENTS

| | | | | |
|---|---|---|---|---|
| 2,910,606 A * | 10/1959 | Suter | ...................... | 313/131 R |
| 4,604,680 A * | 8/1986 | Levin et al. | ................. | 362/293 |
| 4,734,612 A * | 3/1988 | Sasaki et al. | .................... | 313/15 |
| 4,864,180 A * | 9/1989 | English et al. | ................. | 313/44 |
| 5,438,233 A * | 8/1995 | Boland et al. | ............... | 313/110 |
| 5,610,469 A * | 3/1997 | Bergman et al. | ............... | 313/25 |
| 5,838,016 A * | 11/1998 | Johnson | .................. | 250/504 R |
| 5,838,104 A * | 11/1998 | Rutan et al. | ................. | 313/560 |
| 5,939,726 A * | 8/1999 | Wood | ...................... | 250/504 R |
| 6,469,443 B1 * | 10/2002 | Bryant et al. | ................ | 313/636 |
| 6,472,818 B1 * | 10/2002 | Ikeda et al. | .................. | 313/558 |
| 6,586,878 B1 * | 7/2003 | Tu | .............................. | 313/549 |
| 6,777,701 B1 * | 8/2004 | Inbar | ....................... | 250/504 R |

* cited by examiner

*Primary Examiner*—Nikita Wells
*Assistant Examiner*—Anthony Quash
(74) *Attorney, Agent, or Firm*—Craig M. Stainbrook; Stainbrook & Stainbrook, LLP (57) ABSTRACT

An emitting source capable of radiating substantial energy in the near infrared spectrum and suitable for use in non-dispersive infrared gas analyzers or other devices is described. Operation can be steady state (DC) or pulsed at high frequency with excellent modulation characteristics. The device consists of a tungsten filament mounted across the pins of a small transistor outline header and centered at the focal point of a parabolic or other shaped reflector. The header assembly is enclosed by a resistance-welded cap and window assembly having a specially sealed sapphire or other suitable IR transmissive window. Fundamental to the operation of the inventive IR emitter is the incorporation of a getter within the header package configured to prevent oxidation degradation of the tungsten filament. An inert gas backfill limits filament evaporation and further extends apparatus lifetime.

26 Claims, 6 Drawing Sheets

INFRARED RADIATION EMITTER

CROSS REFERENCE TO RELATED APPLICATIONS

The present application claims the benefit of the filing dates of U.S. Provisional Patent Application Ser. No. 60/537,826, filed Jan. 20, 2004, and U.S. Provisional Patent Application Ser. No. 60/473,498, filed May 27, 2003.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The present invention relates generally to infrared radiation sources, and particularly to an emitter which radiates in the near infrared spectrum for use in non-dispersive infrared (NDIR) gas analyzers and other devices requiring an infrared source.

BACKGROUND INFORMATION AND DISCUSSION OF RELATED ART

It is known to employ infrared (IR) emitters in connection with dispersive and non-dispersive-type infrared spectrometers and gas analyzers. Applications are manifold, including medical and industrial gas detection and analysis. IR sources are employed in the carbon dioxide breath analysis of medical patients, alcohol breath analysis by law enforcement personnel, refrigerant gas leak detection, CO analysis for car exhaust, and so forth. In the various settings, the infrared source is typically a laser, a Nernst or Globar radiator, a semiconductor IR emitting diode, or electrically heated elements, such as wires or foil strips, which emit radiation in the infrared portion of the electromagnetic radiation spectrum. In most analytical systems, means are generally employed to modulate the infrared emission, including mechanical means such as a chopper wheel, whereby the emission is allowed or obstructed according to a predetermined cycle. The modulated beam passes through a sample volume that may include wavelength selective filters and strikes a photo detector which amplifies and conditions the signal for display.

Exemplary and illustrative devices in the prior art include those disclosed and taught in several recently issued U.S. patents, including: U.S. Pat. No. 4,859,859, to Knodle, et al, which discloses an infrared source comprising an electrically modulated, stable thick film mounted on a thin ceramic substrate. The source has good modulation but is limited to very low power.

U.S. Pat. No. 5,342,951 to Kocache et al teaches a miniature source of modulated infra-red energy comprising a very thin heated foil strip of low mass, mounted in a tensioned state by means of two resilient members, and a reflector positioned behind the wire to enhance the radiated energy. The source is hermetically sealed in an inert atmosphere with a cap with a plastic sealed window. The cap has an aperture through which the energy emerges, and which is sealed either with a window or a filter if a specific wavelength emission is desired.

U.S. Pat. No. 5,438,233 to Boland, et al, teaches an infrared lamp having a one-piece hollow body, a tungsten filament that emits broad band IR radiation, an optical window having an aperture for the radiation emission, an indium allow junction between the window and the body to seal the window, a pliable coating overlaying the indium junction and part of the body, and a gas contained within the body to prevent deterioration of the filament. While this device advances significantly over the prior art, an indium seal is fragile and easily broken, and any elastomer (i.e., pliable) coating employed to reduce the fragility will interfere with the use of a heat sink to control the temperature of the lamp. Finally, this lamp, to the knowledge of the present inventor, cannot be pulsed at frequencies useful for nondispersive IR gas analysis.

U.S. Pat. No. 5,838,016 to Johnson shows an IR radiation source comprising a radiation filament having a textured surface produced by seeded ion bombardment of a metal foil which is cut to a serpentine shape and mounted in a windowed housing. Specific ion bombardment texturing techniques tune the surface to maximize emissions in the desired wavelength range and to limit emissions outside that narrow range, particularly at longer wavelengths.

U.S. Pat. No. 5,864,144 to Laine, discloses an infrared (IR) radiation emitting device comprises a sinuous foil resistive element which emits IR radiation when heated by an electric current. The device is configured so that the resistive element emits radiation with a spatial intensity which substantially possesses a single axis. The resistive element may, for example, be configured as a substantially planar spiral.

U.S. Pat. No. 5,939,726 to the present inventor, discloses a pulsable infrared radiation (IR) source which can be used in nondispersive infrared gas analyzers. The pulsable IR source includes a narrow strip of thin metallic foil vertically mounted to the opposite sides of pins of a small transistor type (TO-5 or TO-8) header at the base of a large diameter deep reflector. Infrared radiation from both sides of the heated foil is directly reflected to form a highly efficient source. The foil can be oxidized or otherwise coated under controlled conditions to maximize its emissivity at operating temperatures up to approximately 1200 degrees K. The package is resistance welded with a cap and hermetically sealed window of a suitable material and filter as required to transmit the desired infrared spectrum. An appropriate inert backfill gas prevents further oxidation and enhances the pulsing capability.

U.S. Pat. No. 6,297,511 to Syllaios et al, teaches a high frequently infrared radiation emitter. The emitter includes a low-thermal-mass resistive membrane suspended by long thermal isolation arms over a substrate. The membrane is suspended over the substrate such that a resonant emitting cavity is formed between the membrane and the substrate. The low-mass, thermally isolated membrane design maximizes the temperature change induced by Joule heating of the resistive membrane and allows the emitted IR radiation to be modulated at high frequencies.

The foregoing patents and prior art devices disclosed and, to the knowledge and understanding of the present inventor, all other devices in the prior art, provide IR sources of either limited power or limited pulsability and modulation depth. For example, Cal-Sensors, Inc., of Santa Rosa, Calif., produces an IR emitter that is limited to no more than 727 degrees C. for its pulsable NiCr foil emitters and 900 degrees C. for its Kanthal wire coil steady state sources. Ion Optics, Inc., of Waltham, Mass. manufactures IR emitters limited to approximately 600 degrees C. The radiated power increases as the fourth power of the absolute temperature; thus, increasing the temperature of the filament is the best way to increase the output power. However, NiCr has an extremely short life span when operated above 800 degrees C. Thus the need for a durable and long lasting IR emitter having higher power and greater modulation depth has not been adequately addressed.

Reference to, and discussion of, the background art is intended to aid in discharging Applicant's acknowledged duty of candor in disclosing information that may be relevant to the examination of claims to the present invention. However, it is respectfully submitted that none of the above-indicated patents disclose, teach, suggest, show, or otherwise render obvious, either singly or when considered in combination, the invention described and claimed herein.

BRIEF SUMMARY OF THE INVENTION

The present invention is an infrared radiation emitter that can be operated in either a steady state or a pulsed mode. It is capable of a higher power output in either mode than existing devices in the field, and in the pulsed mode has significantly greater modulation depth at higher frequency and power than known devices at longer wavelengths. Novel features of the present invention include:

(1) use of tungsten filament; in combination with (2) an IR transmissive window, e.g. sapphire (which transmits infrared radiation out to approximately 5 micrometers in wavelength), calcium fluoride (which transmits infrared out to approximately 9 micrometers in wavelength), or ZnSe (which transmits infrared out to approximately 14 micrometers in wavelength); in combination with (3) an $O_2$ getter (to prevent oxidation and hence premature failure of the filament); further in combination with (4) a secondary fine wire filament to heat, and therefore activate, the getter after the package is sealed; further in combination with (5) a gold-plated, aluminum, or aluminum-plated parabolic or elliptically shaped reflector; further in combination with (6) $N_2$, argon, or other inert backfill gas, and finally in combination with (7) an industrial standard TO-style (Transistor Outline) metal package lamp housing (can) with two glass sealed pins.

With respect to the first novel feature noted above, viz. the tungsten filament, it should be noted that even though tungsten has a relatively lower emissivity in the infrared (approximately 0.2) than NiCr (approximately 0.88 fully oxidized), the ability of tungsten to operate at higher temperatures (2800 K and above, compared to 1000 K for NiCr) much more than compensates for this difference, because the radiated power is proportional to the fourth power of the absolute temperature.

Prior art IR sources utilize (1), (2), (6) and (7), but not in combination. For example, Gilway Technical Lamp of Woburn, Mass. makes a tungsten lamp for IR applications, but it utilizes a glass envelope that transmits IR radiation to only about three micrometers in wavelength. Cal-Sensors, Inc, produces an IR lamp with sapphire or ZnSe windows and a polished Aluminum reflector in a TO style package, but the filament is fabricated of Nichrome foil or Kanthal wire and cannot reach the high temperature, and therefore the radiated power, possible with tungsten. Boland utilizes (1), (2), (5), and (6), but the source cannot be pulsed at frequencies useful for nondispersive IR gas analysis.

The IR source is backfilled with nitrogen, argon, or other inert gas or combination of inert gases. The presence of the inert gas(es) suppresses the evaporation rate and generally retards degradation of the tungsten filament by several orders of magnitude of what it would experience in a vacuum. This extends filament lifetime at the rated power or allows operation at higher temperatures for the same nominal lifetime.

$N_2$ is used as the backfill gas for the pulsable source because it has a relatively high thermal conductivity which promotes rapid cooling of the filament during the "OFF" portion of the cycle. Argon is the preferred gas for the steady state source because it has a lower thermal conductivity and assists in preventing heat loss from the filament.

Early efforts of the present inventor to develop a tungsten source employing a tungsten filament inside an industrial standard TO-8 package (with no reflector) were unavailing. In those efforts, sapphire window seals were made with plastic, but after capping the sources burned out in only a few hours. Evidently, residual oxygen in the package or driven from the plastic, or oxygen leaking through the plastic seal, caused the premature failure. Those efforts were quickly terminated, and workable alternatives were not conceived until the present.

It is therefore an object and advantage of the present invention to provide an IR source having higher power with greater modulation depth than presently available. Applications include medical and industrial gas detection and analysis and many other miscellaneous applications such as identification of plastics and trace contaminants in fluids, etc. Having a higher power source with the same detector will increase the overall signal-to-noise ratio and therefore the sensitivity of the measurement instrument. Alternatively, a higher power source will allow the device manufacturer to use a less expensive detector to achieve the same signal-to-noise ratio in the system. This is advantageous because detectors are relatively more expensive than sources, while low sensitivity detectors are relatively less expensive than high sensitivity detectors.

Other novel features which are characteristic of the invention, as to organization and method of operation, together with further objects and advantages thereof will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty that characterize the invention are pointed out with particularity in the claims annexed to and forming part of this disclosure. The invention does not reside in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of this application, which is measured by the claims, nor is it intended to be limiting as to the scope of the invention in any way.

Certain terminology and derivations thereof may be used in the following description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

BRIEF DESCRIPTION OF THE SEVERAL VIEWS OF THE DRAWINGS

The invention will be better understood and objects other than those set forth above will become apparent when consideration is given to the following detailed description thereof. Such description makes reference to the annexed drawings wherein.

DRAWING REFERENCE NUMERALS

FIGS. 1–6
100 first preferred embodiment of the present invention, generally
110 header
120 base
125 contact or weld point where reflector 150 is affixed to base 120
130A first electrical input (feed-through) pin
130B second electrical input (feed-through) pin
135 glass seals in base
140 tungsten filament
150 reflector
155 focal point of reflector
157 upper rim of reflector
160 glass bead filament support
170 oxygen getter strip
175 weld point where oxygen getter strip is welded to one of the input pins
180 NiCr wire
200 weld flange (for welding window assembly 300 to base)
205A first cross bar
205B second cross bar
210 filament leads
215 weld points where filament leads are welded to the input pins
220 weld points where NiCr wire is welded between one of the input pins and the header base
300 sapphire, calcium fluoride, or ZnSe cap and window assembly
310 IR transmissive window
320 upper portion of cap 330
330 nickel TO-8 or TO-5 cap
340 hermetic/high vacuum seal
600 second preferred embodiment of the present invention, generally
700 third preferred embodiment of the present invention, generally
710 tungsten filament
720 first electrical input (feed-through) pin
730 electrical input (feed-through) pin
740 header
750 first cross bar
760 second cross bar
770 molybdenum sleeves
780 focal point of reflector
790 reflector
800 oxygen getter strip
810 long axis of the filament
820 optical axis of the reflector

DETAILED DESCRIPTION OF THE INVENTION

Referring to FIGS. 1 through 6, wherein like reference numerals refer to like components in the various views, there is illustrated therein three preferred embodiments of a new and improved infrared radiation emission source, generally denominated herein as 100, 600, and 700, respectively.

Figure 1:
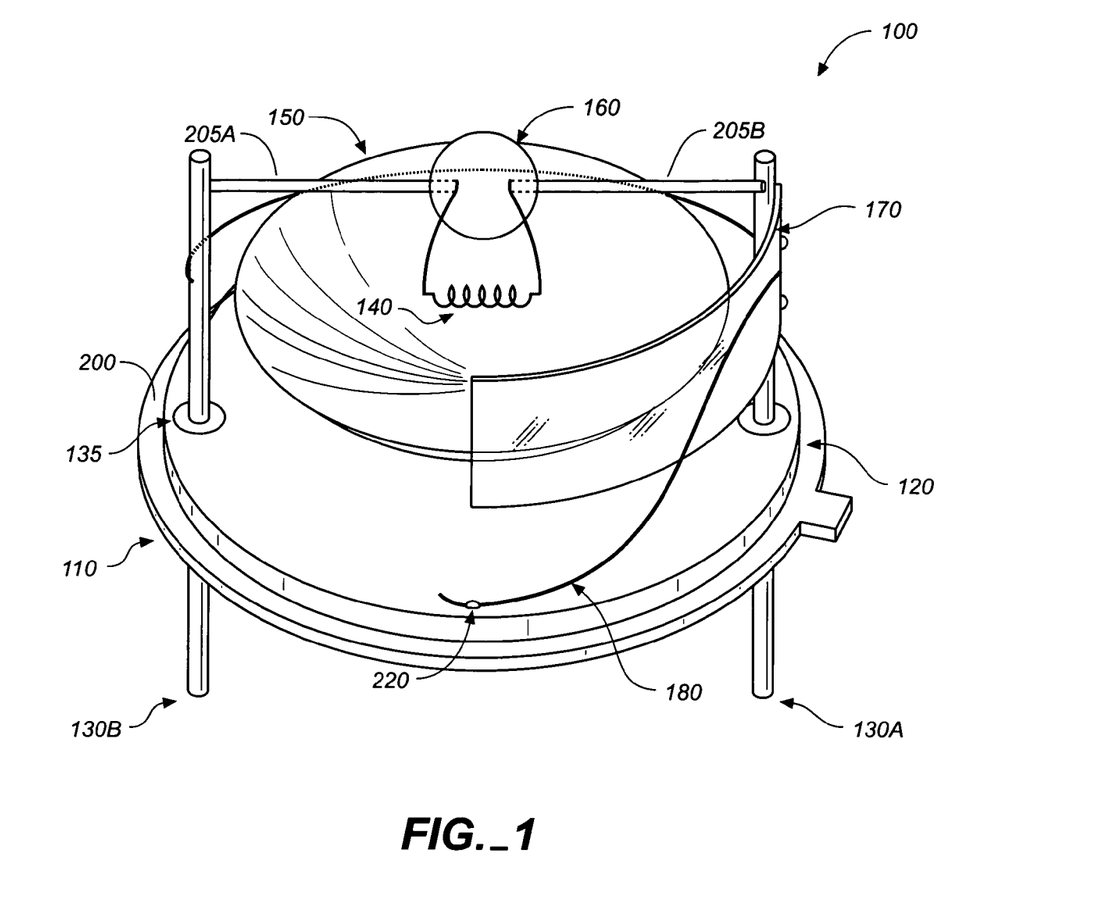
FIG. 1 is a perspective view of the infrared radiation emitter of the present invention.
Figure 2:
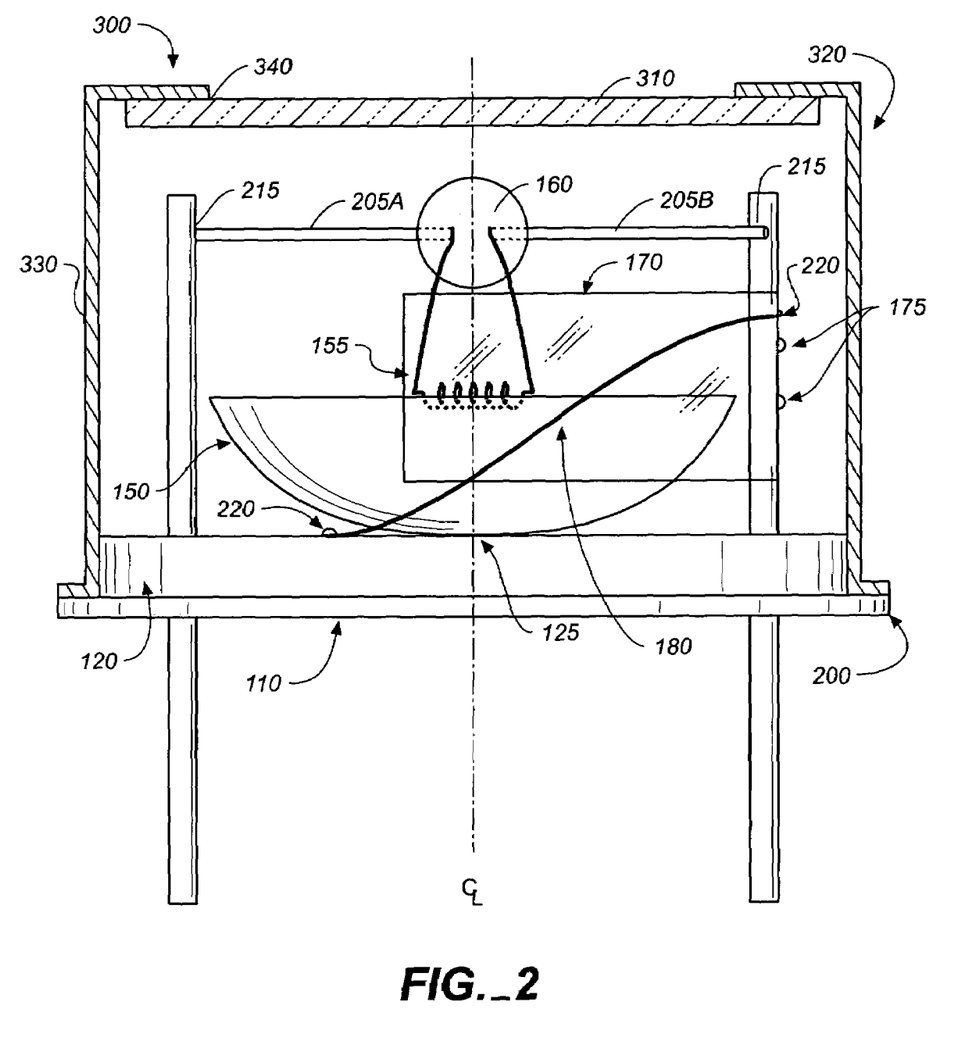
FIG. 2 is a side view in elevation of the apparatus of FIG. 1.
Figure 3:
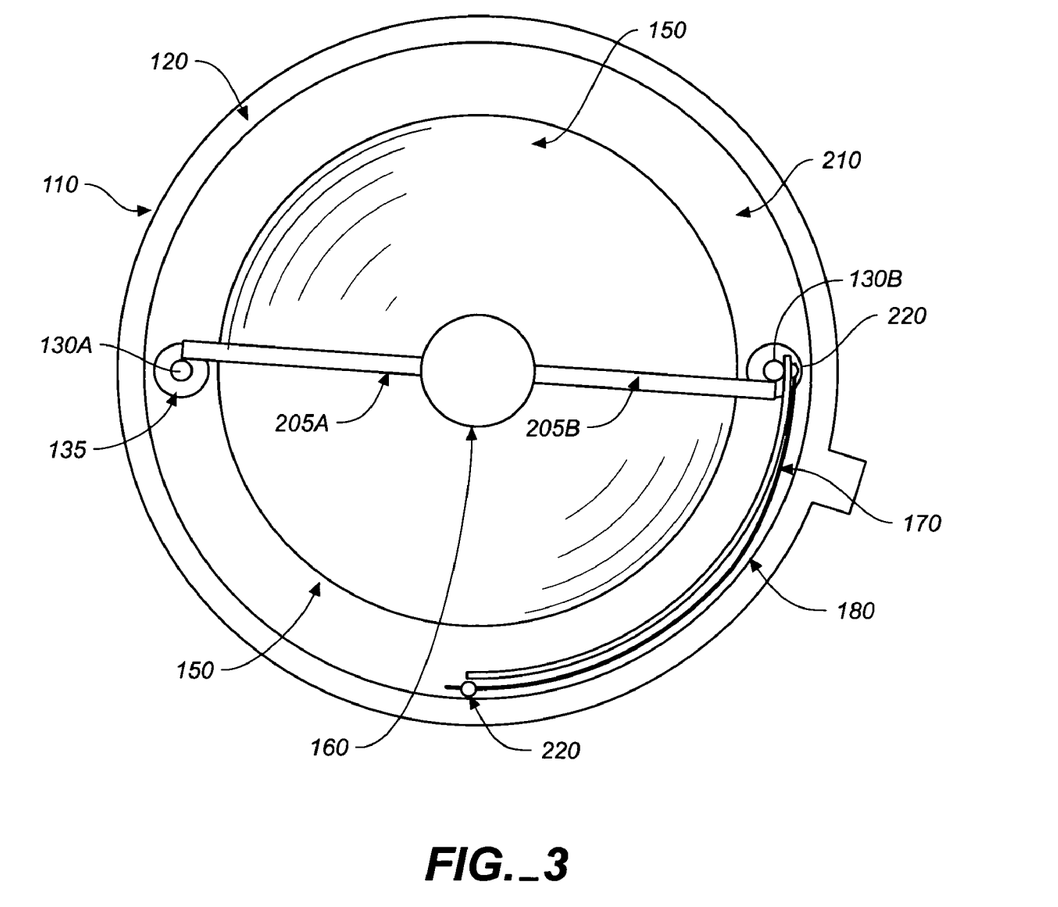
FIG. 3 is a top plan view of the inventive infrared emitter.

FIGS. 1–3 illustrate a first preferred embodiment 100 of the infrared radiation emitter. This embodiment is primarily for use with a pulsable source as it includes delicate tungsten filaments with leads stabilized in a glass bead. These views show that the inventive apparatus includes an industrial standard TO-8 or similar header 110 having a base 120 with first and second electrical input (feed-through) pins 130A, 130B, or simply input pins. The input pins pass through glass seals 135 in the base. The input pins supply electrical current through leads and to a fine looped or coiled tungsten filament 140 suspended above a gold-plated reflecter150 at the reflector's focal point 155 by a glass bead filament support 160. An oxygen getter strip170 and a fine NiCr wire 180 are also disposed on the base, and these elements, along with the tungsten wire, are all covered with a sapphire, calcium fluoride, or zinc selenide (ZnSe) cap and window assembly 300, resistance welded to the base at the weld flange 200, after backfilling with $N_2$, argon, or other inert gas.

The ends of the leads that support the tungsten filament 140 are embedded in the glass bead filament support, and the filament is welded across the two input pins with first and second cross bars 205A, 205B, which are, in turn, welded to the input pins at weld points 215. The cross bars are preferably fabricated from molybdenum (or another compatible high melting point material) and are welded in a straight or curvilinear fashion to the input pins on the header. The cross bars extend inwardly from the input pins generally toward the optical axis (see FIG. 6) of the reflector.

The fine NiCr wire 180, consisting of a small loop or straight wire, is welded at weld points 220 between one of the pins 130A and the header base 120. This loop or coil activates the the oxygen getter strip 170 through proximity. The oxygen getter strip is welded to one of the input pins 130A with at least one weld 175. The reflector 150 is welded or otherwise affixed to the base 120 with at least one weld 125. Manufacturing preferences may dictate that the reflector be attached to the header with adhesives rather than welded. One possible approach is to employ water-based inorganic adhesives that utilize aluminum oxide powder as a filler.

Figure 4:
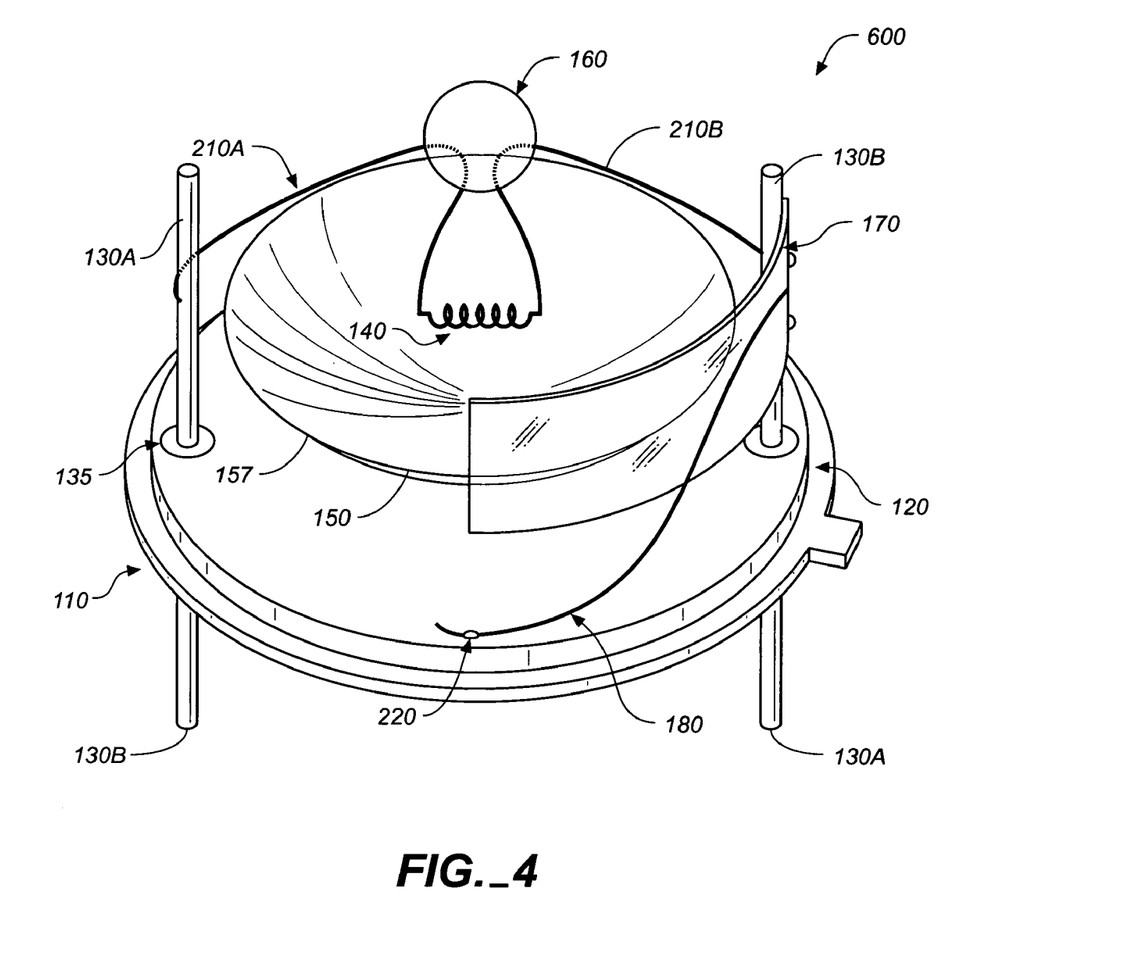
FIG. 4 is a perspective view of an second preferred embodiment of the improved infrared radiation emitter of the present invention.

The cap and window assembly 300 comprises an IR transmissive window 310 (preferably sapphire, calcium fluoride, or zinc selenide), disposed at the upper portion 320 of a nickel TO-8 or TO-5 cap 330 and having a hermetic/high vacuum seal (brazed or with solder) 340. It may be desirable, both for manufacturing ease and performance, to metallize the window and then seal it to the cap with a high temperature solder in a brazed- or solder-seal process. Dimensions of a possible configuration are shown in FIG. 4, though these do not in any way indicate dimensions of emitters embodying all of the inventive features of the present invention.

After the package is sealed, a low voltage is applied between the case and the relevant pin, which, in turn, heats the getter to approximately 250 degrees Centigrade, thereby activating it. After it is activated, the voltage is rapidly increased, and this burns out the filament and opens the circuit so that there is no short between the tungsten filament and the package. Activation is a one-time event that does not require repeating; the small filament can be sacrificed.

The tungsten filament requires an oxygen free environment to survive. Even trace amounts will destroy the filament or greatly decrease the life time. The TO-type metal packages with brazed or solder-sealed windows have very low leak rates, but they are not sealed to the same level as a fully glass-enclosed light bulb. Accordingly, there is always some low level leakage around the pins or through the seals. Therefore, the getter is an essential component. The getter has the ability to absorb oxygen both cold and when heated by the filament. Typically, when the lamp is ON the getter should be positioned such that it has a running temperature of about 200 to 250 degrees C. In this configuration, the tungsten filament should have a lifetime comparable to what it would achieve in a fully glass-enclosed bulb.

Paramount among the novel features of the present invention are the use of tungsten filament and oxygen getter with sapphire, $CaF_2$, or ZnSe window. This novel combination is made possible by using a brazed seal for the sapphire window or a solder seal for the $CaF_2$ or ZnSe. These seals have a very low leak rate, and therefore the getter can absorb the small amount of oxygen that leaks or effuses through the seals. The TO-type can is resistance welded onto the header, and this is virtually leakproof when properly fabricated.

To appreciate the advance in the art represented by the present invention, it should be noted that there is a practical manufacturing challenge in combining a tungsten filament, IR transmissive window, inert gas backfill, and a TO-style housing. This challenge arises from the difficulty in providing a sufficiently secure glass seal around the pins in the header and a sufficiently secure seal around the window to prevent $O_2$ leaks. Such leaks destroy the filament within a very short period of time, perhaps only a day or so.

Even the relatively recent development of brazed sapphire window seals (effective up to approximately $10^{-8}$ Torr vacuum) in combination with TO-style packages would likely not provide a sufficiently adequate seal for long lifetime. The very fine tungsten filaments are extremely sensitive to trace $O_2$ and would rapidly disintegrate. Also, unless the inert backfill gas is extremely pure, there is enough residual $O_2$ to significantly damage the filament and degrade its effectiveness, assuming it was not equipped with a getter prior to energizing the filament.

Residual gas getters were first developed for use in electronic vacuum tubes for radios in the 1930's. They are composed of various materials (e.g., K, Na, Mg, Ca, Sr, or Ba) and remove or "getter" various gases including molecular oxygen. In the early vacuum tubes, getters were either flash vaporized onto the inside wall of the tube or mounted on small loops of wire within the tubes. After the tubes were sealed they were immersed in a high frequency electromagnetic field which by induction caused current to flow in the small wire loops thereby heating and activating the getters. This is a "one-time" operation to remove the initial contaminating gases that may have been contained within the fill gas. After that, the getter removes trace amounts of $O_2$ that might leak into the tube past the glass-to-metal seals.

Currently, getters are used in a variety of applications, such as flat panel display monitors for video monitors and televisions, where the getter acts to protect the emitting filament (pixel) elements from oxygen.

The getter employed in the present invention is specifically designed to remove $O_2$ from a $N_2$ environment. The getter must be activated by first heating it to approximately 250 to 300 degrees C. within the enclosed space of the sealed lamp housing, after which the getter will perform both in a cold and heated state. When cold (i.e., when the lamp is turned OFF) residual $O_2$ is adsorbed onto the surface of the getter. When hot (i.e., when the lamp is turned ON), and the getter is heated by direct radiation from the filament, the $O_2$ is absorbed into the volume of the getter material and the surface is renewed for the next OFF cycle. Thus, the lifetime of the lamp is determined by the size of the getter, which determines the volume of gas that, in total, can be absorbed.

Having just two pins in the TO package is very desirable to limit the opportunities for leaks. To the knowledge and understanding of the present inventor, connecting the fine wire between one pin and the base (or case) is entirely novel. After the getter is activated, burning out the fine wire by temporarily increasing the applied voltage eliminates the short circuit between the pin and the case. A short circuit from one pin to the case would be extremely undesirable (and unacceptable) to a user.

Additionally, to the knowledge and understanding of the present inventor, it is novel to employ getters in TO-style packages for use as IR sources. TO-style packages were specifically developed for use with the earliest transistors (hence, the name Transistor Outline (TO-). They are now used commonly in opto-electronic applications, e.g. for detectors, etc. The technology for sealing these packages is very sophisticated.

Other novel features of the present invention include use of a gold- or aluminum-plated reflector. Gold plating is extremely desirable to reflect IR radiation in the two to fifteen (2 to 15) micrometer wavelength range. It effectively increases the reflectivity by several percent over polished aluminum over this region. However, cost concerns may militate for use of aluminum as a satisfactory substitute, as it is only slightly less reflective than gold at the wavelengths of concern in the contemplated fields of use.

Figure 5:
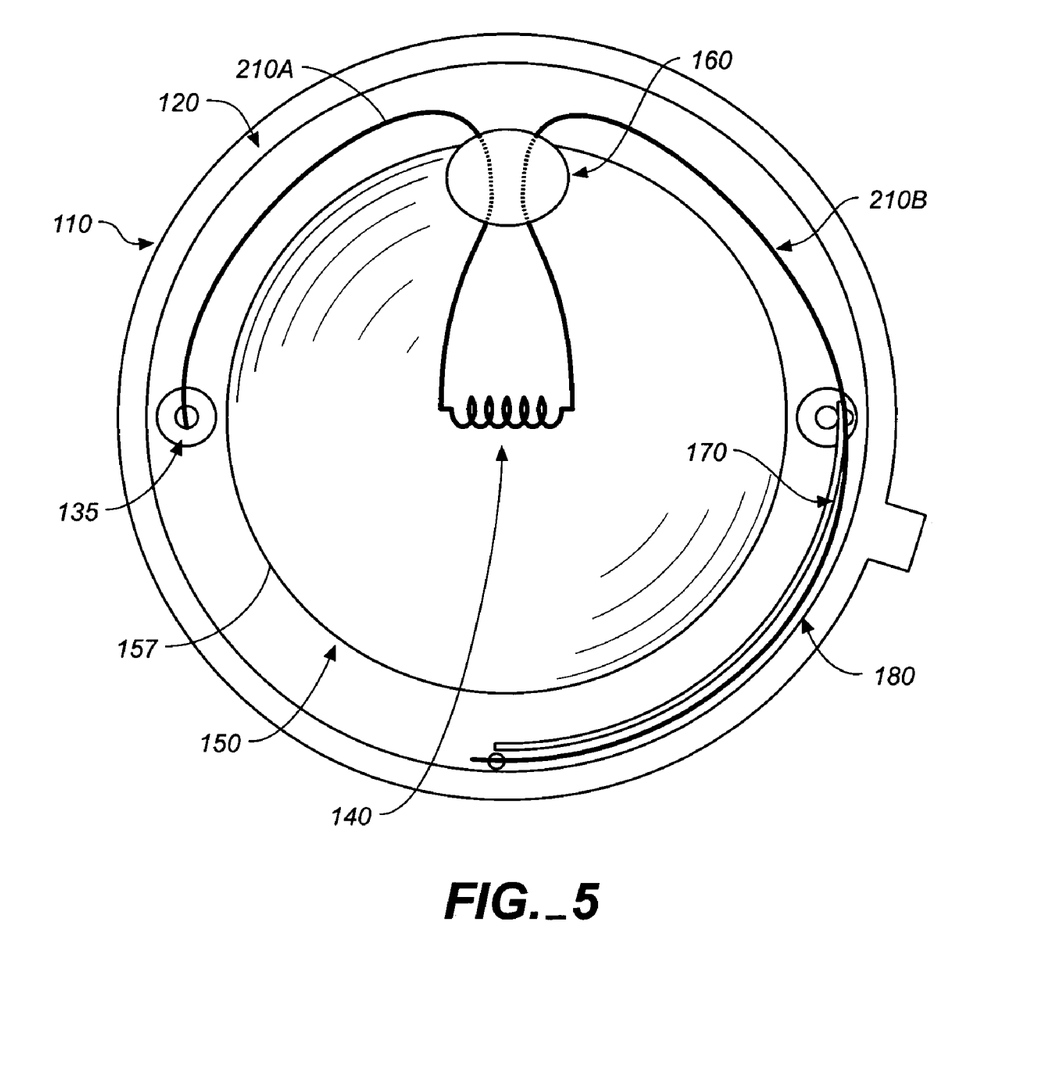
FIG. 5 is a top plan view of the apparatus of FIG. 4.

FIGS. 4–5 show a second preferred embodiment of the present invention. In this embodiment, all of the physical and functional elements are identical to that of the first preferred embodiment, except that the tungsten filament 140 is disposed in a glass bead 160 which is at the edge of reflector 150, rather than immediately above the focal point of the reflector. The tungsten filament then extends inwardly to the focal point 155 of the reflector from the upper rim 157 of the reflector. The tungsten filament is electrically connected to two filament leads 210A, 210B, which are welded or otherwise electrically connected to first and second input pins 130A, 130B.

Figure 6:
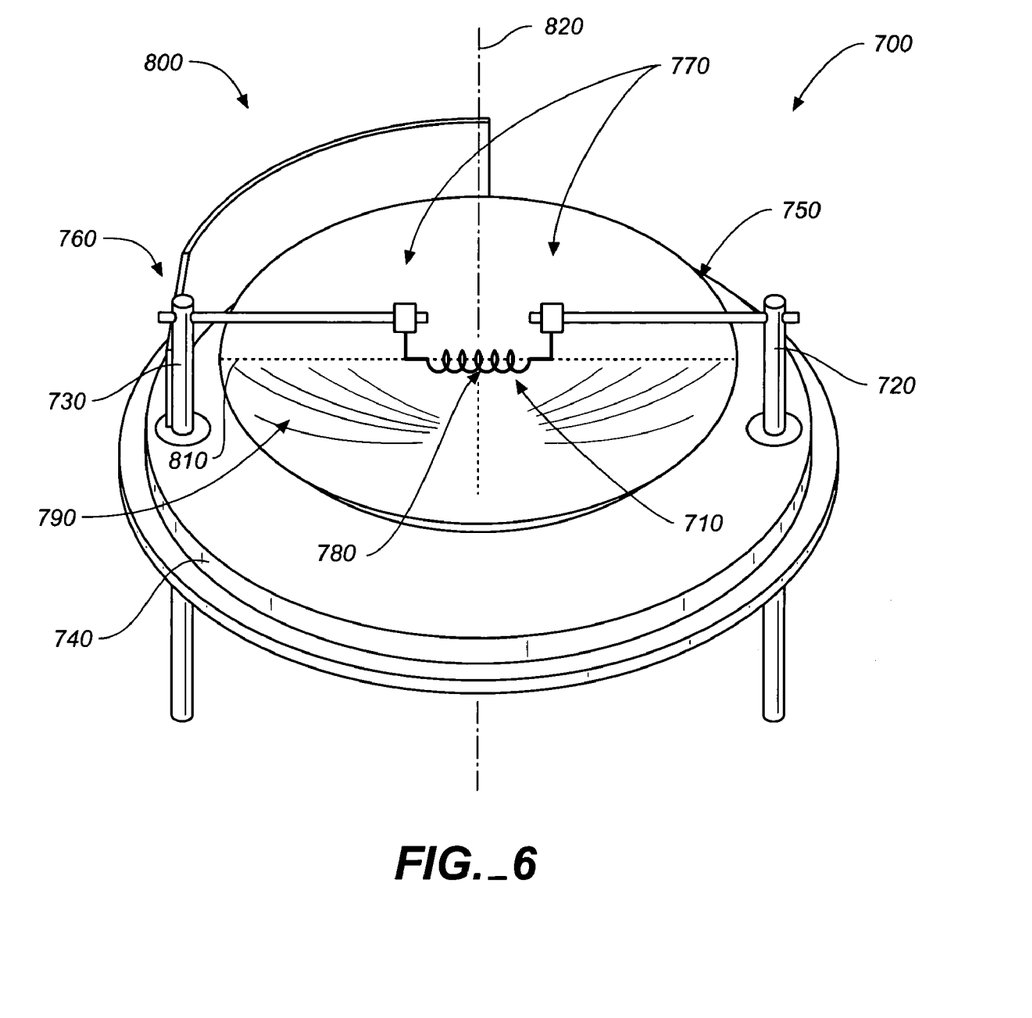
FIG. 6 is a perspective view showing a third preferred embodiment of the inventive apparatus.

FIG. 6 shows a third preferred embodiment 700 of the improved infrared radiation emission source of the present invention. This embodiment is primarily for higher power steady state sources containing larger tungsten filaments and employs a different configuration for mounting the tungsten filament coil 710 to the electrical input (feed-through) pins 720, 730, on the header 740. Again, cross bars 750, 760, preferably fabricated from molybdenum, are welded to the input pins on the header in the manner described above. The tungsten filament is attached to the cross bars by compressing small molybdenum sleeves 770 around the ends of the tungsten lead wires so that it makes a tight mechanical connection; then the compressed sleeves are welded to the cross bars. The filament coil 710 is positioned directly below the cross bars at the focal point 780 of the reflector 790. Again, the getter 800 is welded to one of the input pins. Other orientations of the coil and cross bars are possible, For example, the long axis 810 of the filament is shown to be generally perpendicular to the optical axis 820 of the reflector. However, the filament could be oriented parallel to the optical axis of the reflector.

In manufacture, due to the difference in melting points between tungsten and molybdenum, some kind of mechanical connection is typically made. For instance, the ends of the molybdenum leads can be folded over onto themselves to crimp the tungsten leads; the tungsten leads can be swaged into the molybdenum, or molybdenum sleeves can be used, as in the second preferred embodiment. However, any of these basis processes can be employed, and they are well known in the industry. Alternatively, the leads can be electrically welded with specialized equipment to prevent recrystallization of the tungsten leads.

It will also be appreciated by those with skill in the art that the NiCr wire which activates the oxygen getter strip may not be necessary. If larger, thicker filaments are employed, sufficient heat may be generated by the filament to activate the getter before filament deterioration occurs. When smaller and finer filaments are employed, the activating wire may be required due to insufficient heat generation.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. For instance, such changes might involve alternative materials, components, structural arrangements, sizes, shapes, forms, functions, operational features or the like. It will be obvious to those with skill in the art that alternative constructions might include: a header with four pins, two for the tungsten filament and two for the NiCr filament. It would be possible to employ three pins with one common, albeit by sacrificing the advantage of minimizing the glass-to-metal seals around pins that are so vulnerable to leakage. It would further be obvious to those skilled in the art to employ different materials for use in the reflector, such as aluminum or aluminum plating, or for the getter-activating filament, such as Kanthal. Further, alternative backfill gases could be employed, such as $N_2$, argon, helium, or other higher molecular weight gases, such as krypton or xenon. It seems possible, though undesirable, to eliminate the secondary (fine NiCr) filament to activate the getter. And a different size or type of package could be employed and still have the appropriate sapphire, $CaF_2$, or ZnSe to metal seals.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

The invention claimed is:

1. An infrared radiation emitter, comprising:
    a header having a base;
    first and second input pins;
    a reflector attached to said base and having a focal point and an optical axis;
    a tungsten wire having ends, said tungsten wire suspended above said reflector;
    leads electrically connecting said tungsten wire to said input pins;
    a cap and window assembly attached to said base, said window assembly including a cap and an IR transmissive window hermetically sealed with a vacuum tight seal to said cap to form a sealed chamber, said cap and window assembly attached to said base such that said transmissive window is disposed above said tungsten wire and such that when electrical current is applied to said input pins, said tungsten wire emits infrared light, wherein the infrared light is gathered by said reflector and directed through said transmissive window along said optical axis;
    an oxygen absorbing getter strip, which, when activated, evacuates oxygen from said sealed chamber and thereby prevents oxidation of said tungsten wire, said getter strip welded to at least one of said first and second input pins; and
    an inert gas backfill contained within said sealed chamber; and a getter-activating filament electrically connected to one of said input pins and to said base and disposed so as to be in close physical proximity with said oxygen absorbing getter strip.

2. The apparatus of claim 1, wherein said getter-activating filament activates said oxygen absorbing getter strip only one time when electrical current is passed through said getter-activating filament.

3. The apparatus of claim 2, wherein said getter-activating filament is selected from the group consisting of NiCr and kanthal wire.

4. The apparatus of claim 1, wherein said header is a TO-type header.

5. The apparatus of claim 1, wherein said reflector is gold-plated.

6. The apparatus of claim 1, wherein said reflector is aluminum or aluminum-plated.

7. The apparatus of claim 1, wherein said reflector is parabolic.

8. The apparatus of claim 1, wherein said reflector is elliptically shaped.

9. The apparatus of claim 1, wherein said tungsten wire is a fine wire filament.

10. The apparatus of claim 1, wherein said inert gas is selected from the group consisting of nitrogen, helium, argon, krypton, and xenon.

11. The apparatus of claim 1, further including a glass bead in which said tungsten filament is stabilized.

12. The apparatus of claim 1, wherein said leads comprise first and second cross bars are welded to said first and second input pins, respectively.

13. The apparatus of claim 12, wherein said cross bars are molybdenum and extend inwardly from said input pins generally toward said optical axis of said reflector.

14. The apparatus of claim 13, wherein said tungsten filament ends are attached to said first and second cross bars with molybdenum sleeves compressed and welded to around said first and second cross bars.

15. The apparatus of claim 1, wherein said leads comprise wires in said base of said header.

16. The apparatus of claim 1, wherein said tungsten filament is suspended above said reflector at substantially said focal point.

17. The apparatus of claim 1, wherein said IR transmissive window is disposed above said focal point in line with said optical axis.

18. The apparatus of claim 1, wherein said IR transmissive window is fabricated from material selected from the group consisting of sapphire, calcium fluoride, and zinc selenium.

19. The apparatus of claim 1, wherein said base includes a flange, and wherein said cap and window assembly is welded to said flange.

20. The apparatus of claim 1, wherein said reflector is attached to said base with an inorganic adhesive.

21. The apparatus of claim 1, wherein said IR transmissive window is attached to said cap with either a solder seal or a brazed seal.

22. The apparatus of claim 1, wherein said first and second input pins pass through said base.

23. A method of making an improved infrared radiation emitter, comprising the steps of:
providing a header having a base;
providing first and second input pins in a spaced-apart relationship;
providing a reflector and attaching it to the base;
connecting a first lead to one input pin and another lead to the other input pin;
connecting a tungsten wire at one end to one of the leads and at another end to the other lead in such a way that the tungsten wire is suspended above the reflector;
welding an oxygen getter strip to at least one of the first and second input pins;
connecting a getter-activating filament at one end to one of the input pins and at another end to the base and positioning it so that it is close physical proximity with the oxygen getter strip;
sealing a cap and window assembly to the base to form a sealed chamber, the cap and window assembly including an IR transmissive window disposed above the tungsten filament;
backfilling the sealed chamber with an inert gas;
activating the oxygen getter strip by passing an electrical current through the getter-activating filament, such tat heat from the getter-activating filament heats the oxygen absorbing getter so that residual oxygen in the package is absorbed prior to operating the tungsten wire wherein when a current is applied to the input pins, the tungsten wire emits infrared light which is directed through the transmissive window.

24. The method of claim 23, further including the step of activating the getter strip by applying a low voltage between said base and said input pins to which said getter-activating filament is connected.

25. The method of claim 23, further including the step of passing the input pins through the base of the header.

26. The method of claim 23, wherein said step of activating the oxygen getter strip includes rapidly increasing the voltage passed through the getter activating filament to cause it to burn it out and open the electrical circuit between the input pins.

* * * * *

UNITED STATES PATENT AND TRADEMARK OFFICE
CERTIFICATE OF CORRECTION

| | | |
|---|---|---|
| PATENT NO. | : 7,122,815 B2 | Page 1 of 2 |
| APPLICATION NO. | : 10/857140 | |
| DATED | : October 17, 2006 | |
| INVENTOR(S) | : Donald S. Wood | |

It is certified that error appears in the above-identified patent and that said Letters Patent is hereby corrected as shown below:

Title Page

Correction to Illustrative Figure

The title page, showing an illustrative figure, should be deleted and substitute therefor the attached title sheet Signed and Sealed this Third Day of April, 2007

JON W. DUDAS
*Director of the United States Patent and Trademark Office*

United States Patent
Wood (10) Patent No.: US 7,122,815 B2
(45) Date of Patent: Oct. 17, 2006

(54) INFRARED RADIATION EMITTER

(76) Inventor: Donald S. Wood, 702 Monroe St., Santa Rosa, CA (US) 95404

(*) Notice: Subject to any disclaimer, the term of this patent is extended or adjusted under 35 U.S.C. 154(b) by 0 days.

(21) Appl. No.: 10/857,140

(22) Filed: May 27, 2004

(65) Prior Publication Data
US 2004/0238763 A1    Dec. 2, 2004

Related U.S. Application Data

(60) Provisional application No. 60/537,826, filed on Jan. 20, 2004, provisional application No. 60/473,498, filed on May 27, 2003.

(51) Int. Cl.
*A61N 5/06*    (2006.01)
(52) U.S. Cl. ............... 250/504 R; 250/504; 250/504 H
(58) Field of Classification Search ............... 250/504, 250/504 R, 504 H, 493.1, 495.1
See application file for complete search history.

(56) References Cited

U.S. PATENT DOCUMENTS

| | | | | |
|---|---|---|---|---|
| 2,910,606 A | * | 10/1959 | Suter | 313/131 R |
| 4,604,680 A | * | 8/1986 | Levin et al. | 362/293 |
| 4,734,612 A | * | 3/1988 | Sasaki et al. | 313/15 |
| 4,864,180 A | * | 9/1989 | English et al. | 313/44 |
| 5,438,233 A | * | 8/1995 | Boland et al. | 313/110 |
| 5,610,469 A | * | 3/1997 | Bergman et al. | 313/25 |
| 5,838,016 A | * | 11/1998 | Johnson | 250/504 R |
| 5,838,104 A | * | 11/1998 | Ratan et al. | 313/560 |
| 5,939,726 A | * | 8/1999 | Wood | 250/504 R |
| 6,469,443 B1 | * | 10/2002 | Bryant et al. | 313/636 |
| 6,472,818 B1 | * | 10/2002 | Ikeda et al. | 313/558 |
| 6,586,878 B1 | * | 7/2003 | Tu | 313/549 |
| 6,777,701 B1 | * | 8/2004 | Inber | 250/504 R |

* cited by examiner

*Primary Examiner*—Nikita Wells
*Assistant Examiner*—Anthony Quash
(74) *Attorney, Agent, or Firm*—Craig M. Stainbrook; Stainbrook & Stainbrook, LLP (57) ABSTRACT

An emitting source capable of radiating substantial energy in the near infrared spectrum and suitable for use in non-dispersive infrared gas analyzers or other devices is described. Operation can be steady state (DC) or pulsed at high frequency with excellent modulation characteristics. The device consists of a tungsten filament mounted across the pins of a small transistor outline header and centered at the focal point of a parabolic or other shaped reflector. The header assembly is enclosed by a resistance-welded cap and window assembly having a specially sealed sapphire or other suitable IR transmissive window. Fundamental to the operation of the inventive IR emitter is the incorporation of a getter within the header package configured to prevent oxidation degradation of the tungsten filament. An inert gas backfill limits filament evaporation and further extends apparatus lifetime.

26 Claims, 6 Drawing Sheets

UNITED STATES PATENT AND TRADEMARK OFFICE
CERTIFICATE OF CORRECTION

| | | |
|---|---|---|
| PATENT NO. | : 7,122,815 B2 | |
| APPLICATION NO. | : 10/857140 | |
| DATED | : October 17, 2006 | |
| INVENTOR(S) | : Donald S. Wood | |

It is certified that error appears in the above-identified patent and that said Letters Patent is hereby corrected as shown below:

Delete fig. 1 and replace with the attached Figure 1, which more essentially illustrates the invention;

Lines 49 through 53, in Column 9, are deleted, as redundant;

In Column 2, Line 5, the word "allow", is corrected to read --alloy--;

In Column 8, Line 62, the word, "militate", is corrected to read, --mitigate--;

In Column 9, Line 38, the word, "basis", is corrected to read, --basic--; and

In Column 12, Line 27, the word, "tat", is corrected to read, --that--.

Signed and Sealed this

First Day of January, 2008

JON W. DUDAS
*Director of the United States Patent and Trademark Office*

FIG._1